US012605510B2

(12) United States Patent
Pitulat et al.

(10) Patent No.: US 12,605,510 B2
(45) Date of Patent: Apr. 21, 2026

(54) PLUNGER ROD AND SYRINGE INCLUDING SAME

(71) Applicant: Becton Dickinson France, Le Pont-de-Claix (FR)

(72) Inventors: Loïc Pitulat, Vaulnaveys le Haut (FR); Yves-Eric Dufour, Meylan (FR)

(73) Assignee: Becton Dickinson France, Le Pont-de-Claix (FR)

( * ) Notice: Subject to any disclaimer, the term of this patent is extended or adjusted under 35 U.S.C. 154(b) by 856 days.

(21) Appl. No.: 17/910,851

(22) PCT Filed: Mar. 10, 2021

(86) PCT No.: PCT/EP2021/056121

§ 371 (c)(1),
(2) Date: Sep. 12, 2022

(87) PCT Pub. No.: WO2021/180824

PCT Pub. Date: Sep. 16, 2021

(65) Prior Publication Data

US 2023/0103772 A1 Apr. 6, 2023

(30) Foreign Application Priority Data

Mar. 11, 2020 (EP) ..................................... 20305250

(51) Int. Cl.
*A61M 5/315* (2006.01)
(52) U.S. Cl.
CPC .................. *A61M 5/31511* (2013.01); *A61M 2005/31518* (2013.01)

(58) Field of Classification Search
CPC ........ A61M 2005/31518; A61M 5/315; A61M 5/31511; A61M 5/31515
See application file for complete search history.

(56) References Cited

U.S. PATENT DOCUMENTS

| | | | |
|---|---|---|---|
| 4,850,958 A | 7/1989 | Berry et al. | |
| 5,135,495 A | 8/1992 | Arcusin | |
| 7,972,312 B2 * | 7/2011 | Koopman | .......... A61M 5/31511 600/432 |
| 9,192,725 B2 | 11/2015 | Kawamura | |
| 2004/0059294 A1 | 3/2004 | Pelkey et al. | |
| 2006/0229568 A1 | 10/2006 | Koopman | |

(Continued)

FOREIGN PATENT DOCUMENTS

| | | |
|---|---|---|
| CN | 1048806 A | 1/1991 |
| CN | 1694743 A | 11/2005 |

(Continued)

*Primary Examiner* — Shefali D Patel
(74) *Attorney, Agent, or Firm* — The Webb Law Firm

(57) ABSTRACT

A plunger rod is for use with a syringe having a syringe barrel. The plunger rod includes an elongated body having a proximal end, a distal end opposite the proximal end, a central axis extending between the proximal end and the distal end, a first curved end face, a second curved end face, and a joining portion joining the first curved end face to the second curved end face. Each of the first curved end face, the second curved end face, and the joining portion extends between the proximal end and the distal end. The first curved end face and the second curved end face together are comprised in a circle defined by an outer perimeter of the elongated body.

25 Claims, 8 Drawing Sheets

(56)          References Cited

U.S. PATENT DOCUMENTS

| | | | |
|---|---|---|---|
| 2009/0318880 | A1 | 12/2009 | Janish |
| 2011/0009829 | A1 | 1/2011 | Kosinski et al. |
| 2011/0034882 | A1 | 2/2011 | Quinn et al. |
| 2013/0116628 | A1 | 5/2013 | Kulshrestha et al. |
| 2015/0047631 | A1 | 2/2015 | Norebring |
| 2016/0325047 | A1 | 11/2016 | Vedrine et al. |
| 2016/0325048 | A1 | 11/2016 | Berry et al. |

FOREIGN PATENT DOCUMENTS

| | | | | |
|---|---|---|---|---|
| CN | 201213948 | Y | 4/2009 | |
| CN | 202387059 | U | 8/2012 | |
| DE | 19923131 | A1 * | 11/2000 | ........ A61M 5/31511 |
| EP | 0758255 | B1 | 8/2002 | |
| JP | S6443268 | A | 2/1989 | |
| JP | 2001314506 | A | 11/2001 | |
| JP | 2009142508 | A | 7/2009 | |
| JP | 2013116289 | A | 6/2013 | |
| JP | 3194753 | A | 12/2014 | |
| WO | 2007056773 | A2 | 5/2007 | |
| WO | 2009061315 | A1 | 5/2009 | |
| WO | 2014122782 | A1 | 8/2014 | |

* cited by examiner

PLUNGER ROD AND SYRINGE INCLUDING SAME

CROSS REFERENCE TO RELATED APPLICATIONS

This application is the United States national phase of International Application No. PCT/EP2021/056121 filed Mar. 10, 2021, and claims priority to Europe Patent Application 20305250.1 filed Mar. 11, 2020, the entire disclosures of which are hereby incorporated by reference in their entirety.

BACKGROUND OF THE INVENTION

Field of the Disclosure

The disclosed concept relates generally to a plunger rod for use in a syringe barrel which may be associated with an autoinjector. The disclosed concept further relates to a syringe, such as manual syringe, including a plunger rod assembly.

Description of the Related Art

Syringes, particularly manually operated hypodermic syringes, are well known in the medical field for dispensing fluids, such as medications, or for withdrawing a biological fluid sample therein. A conventional syringe assembly typically includes a syringe barrel with a fluid opening at one end and a plunger assembly disposed through the opposite end, provided in slideable arrangement through the syringe barrel. The plunger assembly typically includes a rigid plunger rod having a linear longitudinal axis extending through the barrel, with a plunger head or stopper located at a distal end of the plunger rod, and with a thumb press provided at the proximal end of the plunger rod. In use, the plunger rod may be retracted through the syringe barrel to aspirate or fill the syringe barrel with a fluid, such as a medicament. The plunger rod may also be advanceable through the syringe barrel to expel a fluid, such as a medicament, from within the syringe barrel. For delivery of medication to a patient, the opening of the syringe barrel may be adapted for fluid communication with a patient, such as through a hypodermic needle fitted at the distal end of the syringe barrel or through a standard luer-type fitting extending from the distal end of the syringe barrel for attachment with a fluid line. Operation of a plunger rod assembly within a syringe barrel is well known in the medical field.

Numerous syringes are used each year in standard medical settings. As a result, it is desirable that the plunger rods of the syringes be manufactured as cost efficiently as possible, be relatively strong (e.g., in order to withstand loads that are applied during use), and be manufactured with a relatively short cycle time during molding. Accordingly, there is a need in the art for such an improved plunger rod and syringe including the same.

SUMMARY

In one aspect, a plunger rod is provided for use with a syringe having a syringe barrel. The plunger includes an elongated body having a proximal end, a distal end opposite the proximal end, a central axis extending between the proximal end and the distal end, a first curved end face, a second curved end face, and a joining portion joining the first curved end face to the second curved end face. Each of the first curved end face, the second curved end face, and the joining portion extends between the proximal end and the distal end. The first curved end face and the second curved end face together are comprised in the circle defined at least partially by an outer perimeter of the elongated body.

In another aspect, a plunger rod is provided for use with a syringe having a syringe barrel. The plunger rod comprises an elongated body having a proximal end, a distal end opposite the proximal end, a central axis extending between the proximal end and the distal end, and a joining portion extending between the proximal end and the distal end, the joining portion at least partially defining an arcuate outer perimeter of the elongated body. The joining portion does not intersect the central axis.

In another aspect, a syringe assembly comprises a syringe barrel having a sidewall, a distal end, and a proximal end; and a plunger rod comprising an elongated body having a proximal end, a distal end opposite the proximal end of the elongated body, a central axis extending between the proximal end of the elongated body and the distal end of the elongated body, a first curved end face, a second curved end face, and a joining portion joining the first curved end face to the second curved end face, each of the first curved end face, the second curved end face, and the joining portion extending between the proximal end of the elongated body and the distal end of the elongated body. The first curved end face and the second curved end face together are comprised in the circle defined by an outer perimeter of the elongated body.

In another aspect, a syringe assembly comprises a syringe barrel having a sidewall, a distal end, and a proximal end; and a plunger rod comprising an elongated body having a proximal end, a distal end opposite the proximal end of the elongated body, a central axis extending between the proximal end of the elongated body and the distal end of the elongated body, a joining portion extending between the proximal end of the elongated body and the distal end of the elongated body, the joining portion at least partially defining an arcuate outer perimeter of the elongated body. The joining portion does not intersect the central axis.

Various other aspects of the present disclosure are recited in one or more of the following clauses:

Clause 1. A plunger rod for use with a syringe having a syringe barrel, the plunger rod comprising: an elongated body having a proximal end, a distal end opposite the proximal end, and a central axis extending between the proximal end and the distal end, a first curved end face, a second curved end face, and a joining portion joining the first curved end face to the second curved end face, each of the first curved end face, the second curved end face, and the joining portion extending between the proximal end and the distal end, wherein the first curved end face and the second curved end face together are comprised in the circle defined by an outer perimeter of the elongated body.

Clause 2. The plunger rod according to clause 1, wherein the joining portion comprises an intermediate face, a first connecting face extending from the intermediate face to the first curved end face, and a second connecting face extending from the intermediate face to the second curved end face, and wherein the intermediate face, the first curved end face, and the second curved end face are comprised in the circle delimited by the outer perimeter of the elongated body together therewith.

Clause 3. The plunger rod according to clause 2, wherein the first connecting face is a first angular face with respect to the intermediate face, and wherein the second connecting face is a second angular face with respect to the intermediate face.

Clause 4. The plunger rod according to clause 3, wherein the first angular face and the second angular face each extend from the intermediate face at respective angles that are equal or greater than 90 degrees with respect to the intermediate face.

Clause 5. The plunger rod according to clause 1, wherein the first curved end face, the second curved end face, and the joining portion do not intersect the central axis of the elongated body.

Clause 6. The plunger rod according to clause 1, wherein the joining portion intersects the central axis and extends directly from first curved end face to the second curved end face.

Clause 7. The plunger rod according to clause 6, wherein the elongated body has a generally S-shaped cross section.

Clause 8. The plunger rod according to clause 1, wherein the plunger rod further comprises a number of support ribs extending from the elongated body between the proximal end and the distal end.

Clause 9. The plunger rod according to clause 1, wherein the arcuate outer perimeter is discontinuous.

Clause 10. A plunger rod for use with a syringe having a syringe barrel, the plunger rod comprising: an elongated body having a proximal end, a distal end opposite the proximal end, and a central axis extending between the proximal end and the distal end, a joining portion extending between the proximal end and the distal end, the joining portion at least partially defining an arcuate outer perimeter of the elongated body, wherein the joining portion does not intersect the central axis.

Clause 11. The plunger rod according to clause 10, wherein the arcuate outer perimeter is concave facing toward the central axis.

Clause 12. The plunger rod according to clause 10, wherein the plunger rod further comprises a number of support ribs extending from the elongated body between the proximal end and the distal end.

Clause 13. The plunger rod according to clause 10, wherein the arcuate outer perimeter is discontinuous.

Clause 14. The plunger rod according to clause 10, further comprising a stopper overmolded onto the elongated body.

Clause 15. A syringe assembly comprising: a syringe barrel having a sidewall, a distal end, and a proximal end; and a plunger rod comprising: an elongated body having a proximal end, a distal end opposite the proximal end of the elongated body, and a central axis extending between the proximal end of the elongated body and the distal end of the elongated body, a first curved end face, a second curved end face, and a joining portion joining the first curved end face to the second curved end face, each of the first curved end face, the second curved end face, and the joining portion extending between the proximal end of the elongated body and the distal end of the elongated body, wherein the first curved end face and the second curved end face together are comprised in the circle defined by an outer perimeter of the elongated body.

Clause 16. The syringe assembly according to clause 15, wherein the joining portion comprises an intermediate face, a first connecting face extending from the intermediate face to the first curved end face, and a second connecting face extending from the intermediate face to the second curved end face, and wherein the intermediate face, the first curved end face, and the second curved end face are comprised in the circle delimited by the outer perimeter of the elongated body together therewith.

Clause 17. The syringe assembly according to clause 16, wherein the first connecting face is a first angular face with respect to the intermediate face, and wherein the second connecting face is a second angular face with respect to the intermediate face.

Clause 18. The syringe assembly according to clause 17, wherein the first angular face and the second angular face each extend from the intermediate face at an angle equal or greater than 90 degrees with respect to the intermediate face.

Clause 19. The syringe assembly according to clause 15, wherein the first curved end face, the second curved end face, and the joining portion do not intersect the central axis of the elongated body.

Clause 20. The syringe assembly according to clause 15, wherein the plunger rod further comprises a thumb press disposed at the proximal end of the elongated body, and wherein the thumb press is wider than the syringe barrel.

Clause 21. The syringe assembly according to clause 15, wherein the plunger rod further comprises a coupling portion disposed at the distal end; and wherein the syringe assembly further comprises a stopper coupled to the coupling portion and disposed internal with respect to the syringe barrel.

Clause 22. The syringe assembly according to clause 15, wherein the arcuate outer perimeter is discontinuous.

Clause 23. A syringe assembly comprising: a syringe barrel having a sidewall, a distal end, and a proximal end; and a plunger rod comprising: an elongated body having a proximal end, a distal end opposite the proximal end of the elongated body, and a central axis extending between the proximal end of the elongated body and the distal end of the elongated body, a joining portion extending between the proximal end of the elongated body and the distal end of the elongated body, the joining portion at least partially defining an arcuate outer perimeter of the elongated body, wherein the joining portion does not intersect the central axis.

Clause 24. The syringe assembly according to clause 23, wherein the arcuate outer perimeter is concave facing toward the central axis.

Clause 25. The syringe assembly according to clause 23, wherein the plunger rod further comprises a thumb press disposed at the proximal end of the elongated body, and wherein the thumb press is wider than the syringe barrel.

Clause 26. The syringe assembly according to clause 23, wherein the plunger rod further comprises a coupling portion disposed at the distal end of the elongated body; and wherein the syringe further comprises a stopper coupled to the coupling portion and disposed internal with respect to the syringe barrel.

Clause 27. The syringe assembly according to clause 23, wherein the arcuate outer perimeter is discontinuous.

Further details and advantages of the various examples described in detail herein will become clear upon reviewing the following detailed description of the various examples in conjunction with the accompanying drawing figures.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
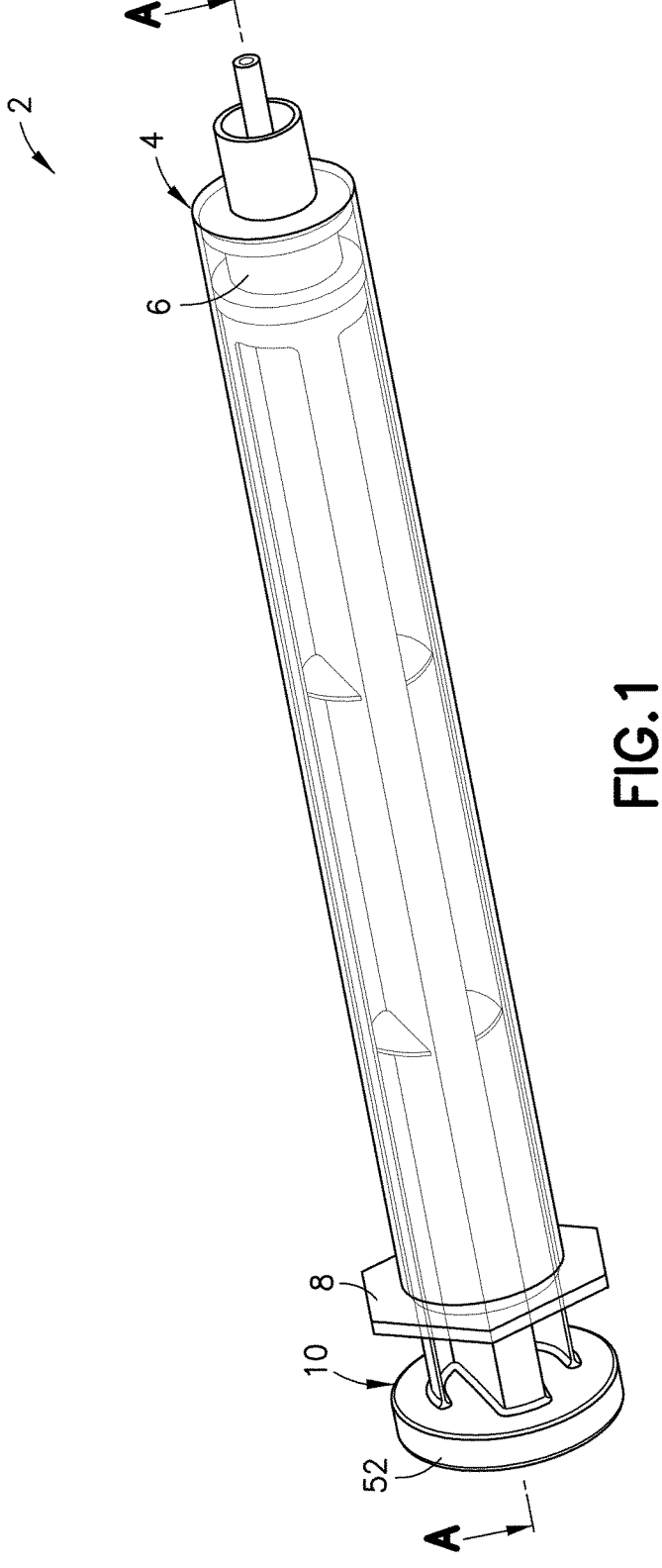
FIG. 1 is a perspective view of a syringe, in accordance with one non-limiting aspect of the disclosed concept.

The following description is provided to enable those skilled in the art to make and use the described embodiments contemplated for carrying out the concept. Various modifications, equivalents, variations, and alternatives, however, will remain readily apparent to those skilled in the art. Any and all such modifications, variations, equivalents, and alternatives are intended to fall within the spirit and scope of the present concept.

For purposes of the description hereinafter, the terms "upper", "lower", "right", "left", "vertical", "horizontal", "top", "bottom", "lateral", "longitudinal", and derivatives thereof shall relate to the concept as it is oriented in the drawing figures. However, it is to be understood that the concept may assume various alternative variations, except where expressly specified to the contrary. It is also to be understood that the specific devices illustrated in the attached drawings, and described in the following specification, are simply exemplary embodiments of the concept. Hence, specific dimensions and other physical characteristics related to the embodiments disclosed herein are not to be considered as limiting.

In the following discussion, "distal" refers to a direction generally toward an end of a syringe assembly adapted for engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

Figure 2:
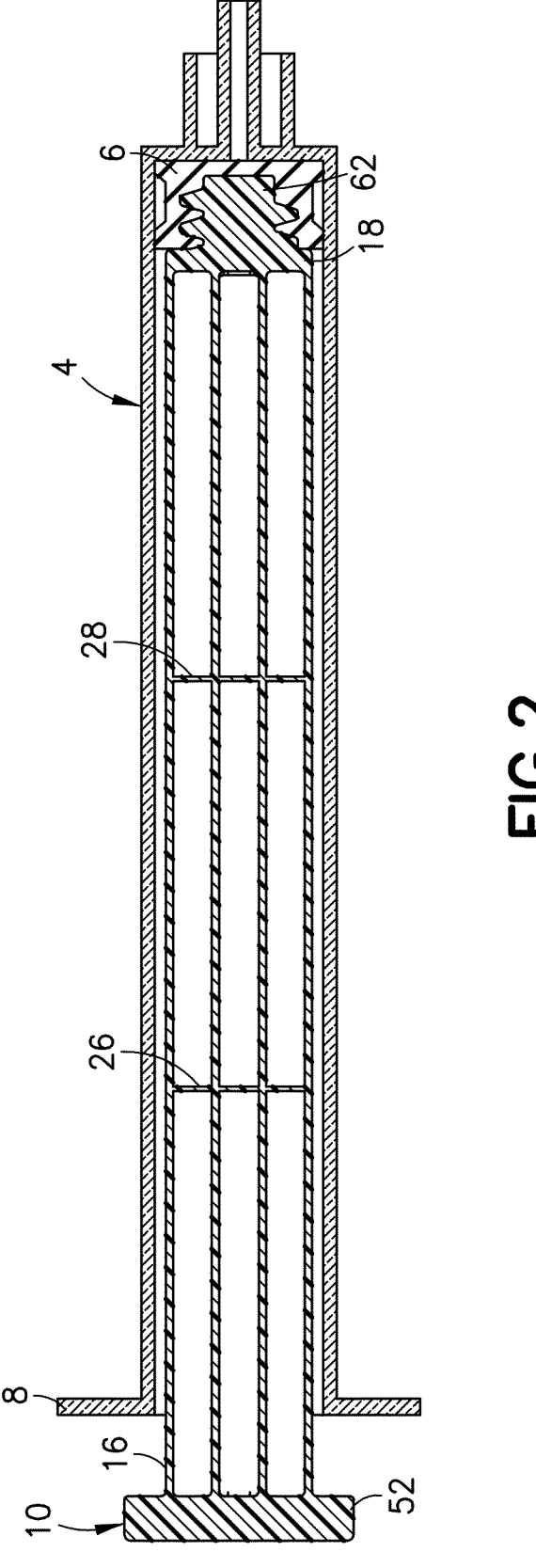
FIG. 2 is a cross-sectional view of the syringe of FIG. 1, taken along line A-A of FIG. 1.

Referring to FIGS. 1 and 2, a syringe assembly 2 includes a syringe barrel 4 having a distal end, a proximal end and a sidewall defining a syringe interior therein. Syringe assembly 2 further includes a piston or stopper 6 positionable within the syringe interior of the syringe barrel 4, a flange 8 extending radially outward from a proximal end of the syringe barrel 4, and a plunger rod 10 insertable within the syringe interior of the syringe barrel 4. In one example embodiment, plunger rod 10 includes stopper 6 which may be overmolded onto an elongated body 12 of plunger rod 10. Stopper 6 may be a polymeric material such as polyurethane (PU), silicon, and a thermoplastic elastomer (TPE). Syringe assembly 2 may be adapted for the dispensing and delivery of a fluid and/or collection of a fluid. For example, syringe assembly 2 may be used for injection or infusion of fluid such as a medication into a patient. The syringe assembly 2 may also be adapted for aspirating a fluid into the syringe barrel 4, such as withdrawing a medication into the syringe interior and/or withdrawing a fluid sample therein. Syringe assembly 2 is contemplated for use in connection with a patient needle, such as by connecting syringe assembly 2 to a separate needle assembly (not shown), or alternatively for connection with an intravenous (IV) connection assembly (not shown). It can be appreciated that the present disclosure can be used with any type of syringe, including those which are placed in a controlled storage environment in which storage space is limited. These types of syringes include traditional pre-filled syringe assemblies, metered dose syringes, aspiration syringes for withdrawing fluid from a patient or medication from a container, and the like.

Figure 3:
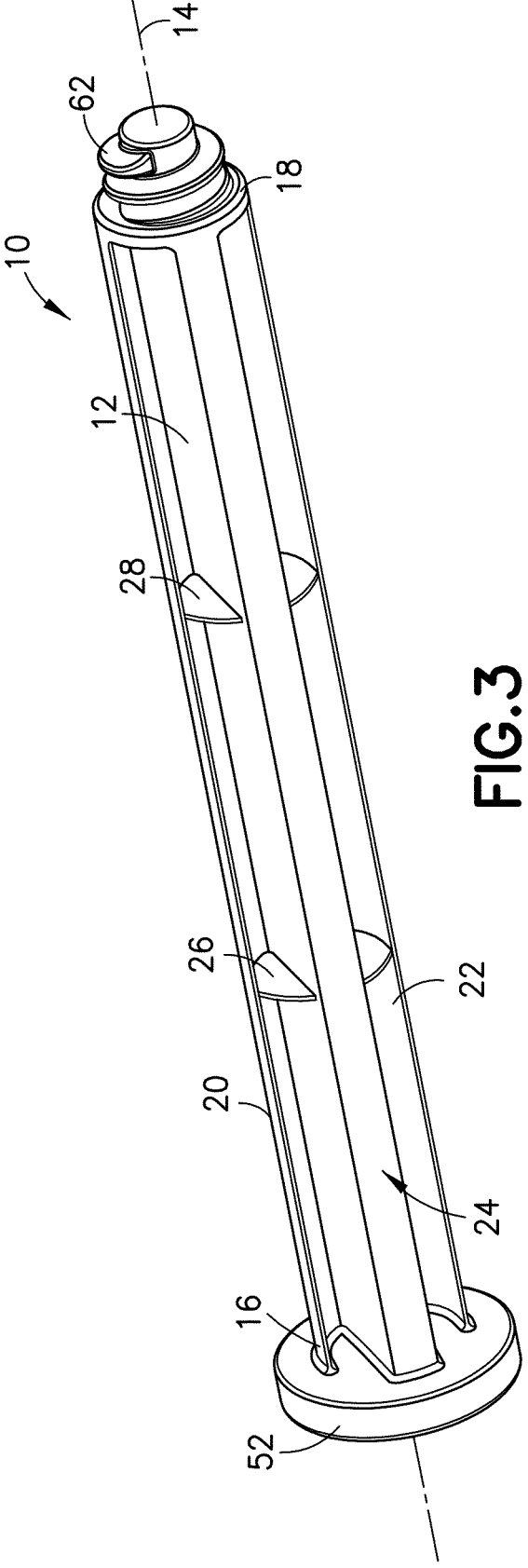
FIG. 3 is a perspective view of a plunger rod for the syringe of FIG. 1.

Structure of the example plunger rod 10 will now be discussed in detail. FIG. 3 shows a perspective view of plunger rod 10. As shown, plunger rod 10 includes an elongated body 12 having a central axis 14 extending between a proximal end 16 and a distal end 18. In one example embodiment, central axis 14 of the plunger rod 10 may coincide with a corresponding central axis of syringe barrel 4. Elongated body 12 of plunger rod 10 has proximal end 16, distal end 18, a first curved end face 20, a second curved end face 22, and a joining portion 24 which joins first curved end face 20 to second curved end face 22. First and second curved end faces 20 and 22 may also be formed of straight line segments or a plurality of corresponding adjacent segments. In one example embodiment, each of first curved end face 20, second curved end face 22, and joining portion 24 extends between proximal end 16 and distal end 18. In one configuration, at least first curved end face 20 and second curved end face 22 together are comprised in the circle defined by an outer perimeter 40 (shown in FIG. 6) of elongated body 12. As shown, the outer perimeter 40 may be discontinuous. As will be discussed below, the improved geometry of plunger rod 10 allows plunger rod 10 to be manufactured with less material, and molded with a smaller cycle time.

Continuing to refer to FIG. 3, plunger rod 10 may optionally further include a thumb press 52 located at proximal end 16 of elongated body 12, and a threaded coupling portion 62 located at distal end 18 of elongated body 12. Thumb press 52 may include a portion that is wider than the interior of the syringe barrel 4 and provides a structure for a user to press when advancing the plunger rod 10 through syringe barrel 4. As shown in FIG. 3, arcuate outer perimeter 40 described above may be lower than the arcuate outer perimeter of the thumb press 52. As shown in FIG. 2, threaded coupling portion 62 may be threadably coupled to a stopper 6. Alternatively, stopper 6 may also be clipped onto plunger rod 10. As a result, this allows plunger rod 10 to advance stopper 6 through syringe barrel 4 as a combined assembly. Furthermore, stopper 6 is sized relative to syringe barrel 4 to provide sealing engagement with the interior surface of the sidewall of syringe barrel 4. It is noted herein that any suitable stopper 6 may be employed with the plunger rod of the present invention.

Elongated body 12 is at least partially disposed within syringe barrel 4 in order to advance stopper 6 through syringe barrel 4. In one embodiment, syringe barrel 4 may be in the general form of an elongated cylindrical barrel as is known in the art in the general shape of a hypodermic syringe. In alternative embodiments, syringe barrel 4 may be in other forms for containing a fluid for delivery. Syringe barrel 4 may be formed of glass, or may be injection molded from thermoplastic material such as polypropylene and polyethylene according to techniques known to those of ordinary skill in the art, though it is to be appreciated that syringe barrel 4 may be made from other suitable materials and according to other applicable techniques.

Figure 4:
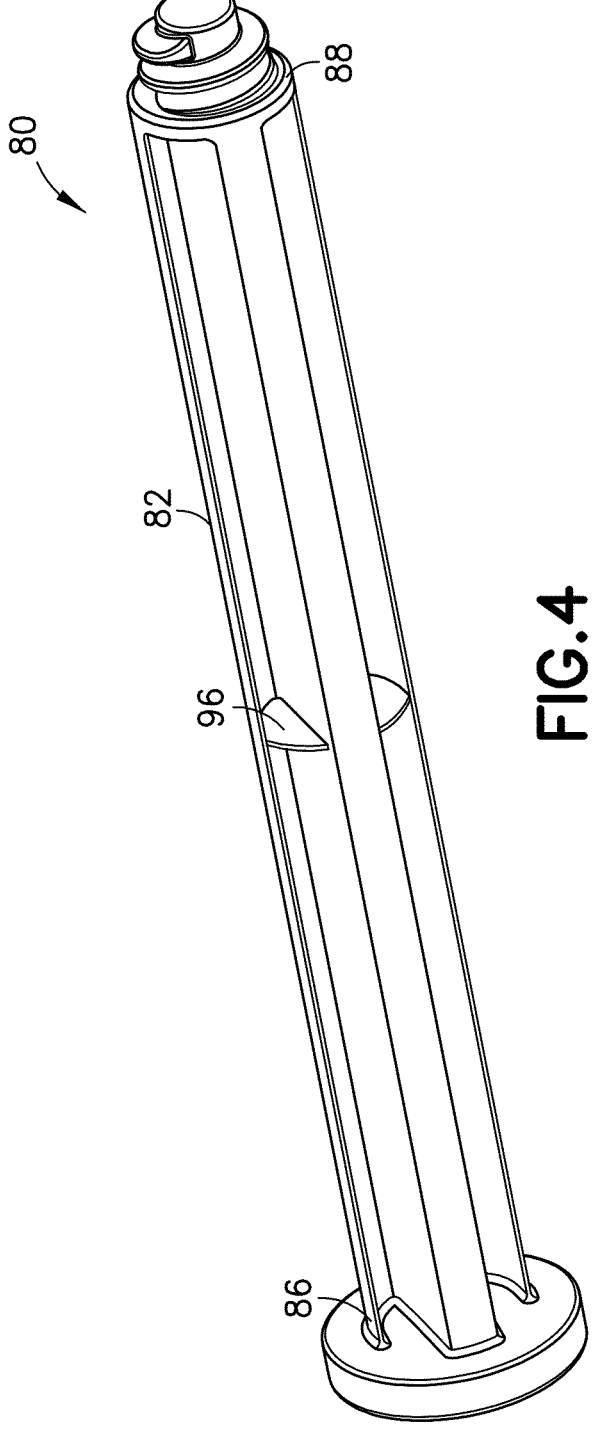
FIG. 4 is a perspective view of another plunger rod that may be used with the syringe of FIG. 1.

In one example embodiment, as shown in FIG. 3, plunger rod 10 further has a plurality of support ribs (two support ribs 26, 28 are shown) extending from elongated body 12 between proximal end 16 and distal end 18. Support ribs 26 and 28 may extend radially, such as orthogonally, with respect to central axis 14, and a plunger rod in accordance with the disclosed concept may include up to five ribs. In another example, as shown in FIG. 4, plunger rod 80 has one single support rib 96 extending from elongated body 82 between proximal end 86 and distal end 88. It will be appreciated that plunger rod 80 otherwise includes all of the same structural features and advantages of plunger rod 10. Support ribs 26, 28, and 96 advantageously function to strengthen and stabilize the plunger rods 10, 80, thereby allowing them to move into and out of syringe barrel 4 without significant and undesirable flexion.

Figure 5:
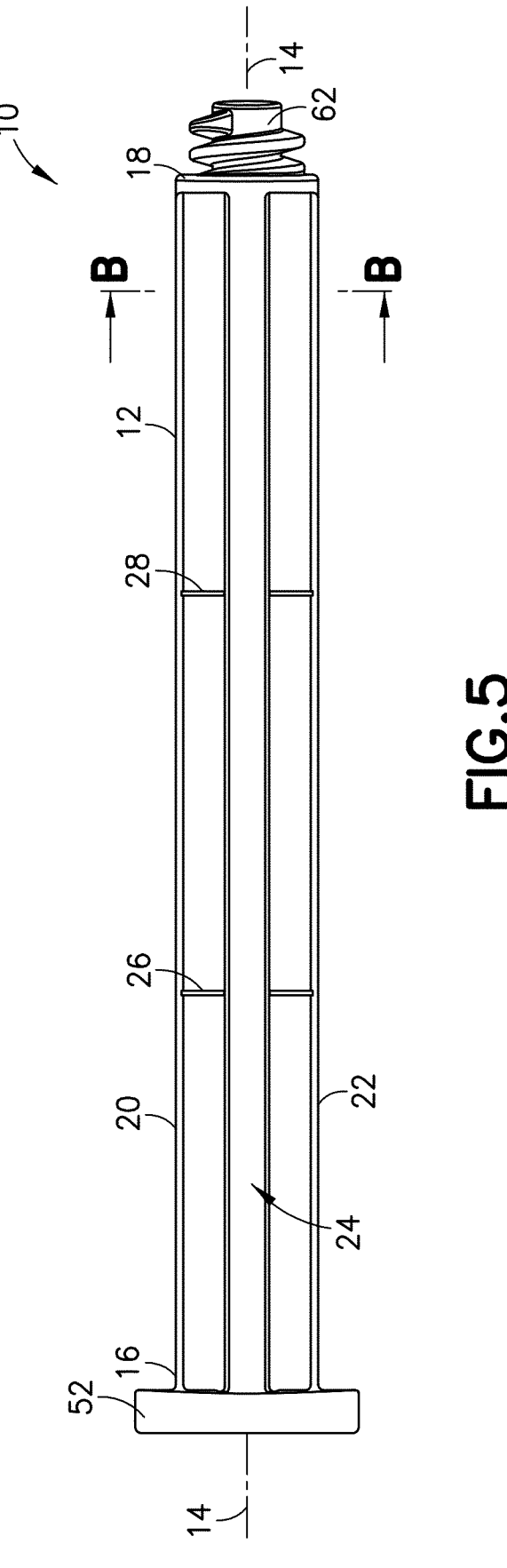
FIG. 5 is a side view of the plunger rod of FIG. 3.
Figure 6:
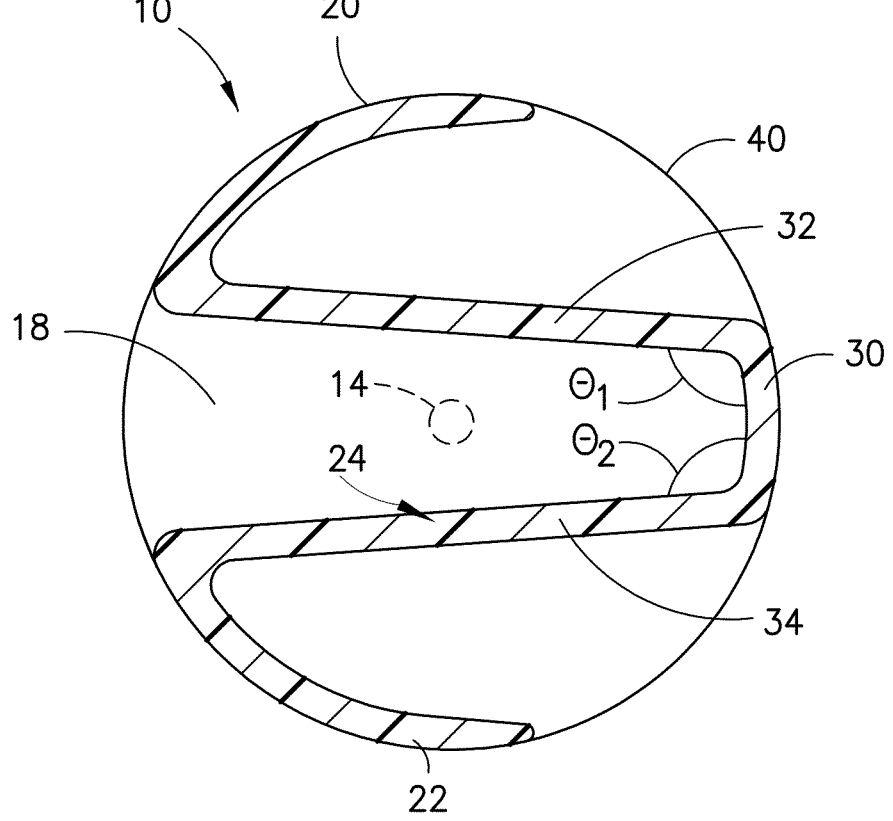
FIG. 6 is a cross-sectional view of the plunger rod of FIG. 5, taken along line B-B of FIG. 5.

FIG. 5 is a side view of plunger rod 10, and FIG. 6 is a cross-sectional view of plunger rod 10. As shown in FIG. 6, joining portion 24 includes an intermediate face 30, a first connecting face (e.g., without limitation, first angular face 32) extending from intermediate face 30 to first curved end face 20, and a second connecting face (e.g., without limitation, second angular face 34) extending from intermediate face 30 to second curved end face 22. Angular faces 32 and 34 may be curved or straight. Joining portion 24 at least partially defines arcuate outer perimeter 40 of elongated body 12, which may be concave facing toward central axis 14. In one example embodiment, intermediate face 30 and curved end faces 20 and 22 are comprised in the circle delimited by the outer perimeter of the elongated body together therewith. Additionally, intermediate face 30 may be curved or straight. Accordingly, it will be appreciated that arcuate outer perimeter 40 may be discontinuous. Furthermore, first and second connecting faces may include first and second angular faces 32, 34, respectively, with respect to intermediate face 30. More specifically, in one example embodiment, first and second angular faces 32, 34 each extend from intermediate face 30 at respective angles $\theta_1$, $\theta_2$, that are equal to or greater than 90 degrees with respect to intermediate face 30. Preferably said angles $\theta_1$, $\theta_2$ are smaller than 120 degrees with respect to intermediate face 30. Additionally, in one configuration, no portion of the first curved end face 20, the second curved end face 22, and/or the joining portion 24 intersect central axis 14 (depicted as a circle in order to represent an axis perpendicular with the page) of elongated body 12. Accordingly, in this configuration, the central axis 14 of the plunger rod 10 is void of material. It is further noted that in certain embodiments, the first curved end face 20 and the second curved end face 22 do not intersect each other, i.e., the first curved end face 20 and the second curved end face 22 do not form a continuous exterior perimeter.

Figures 7, 8:
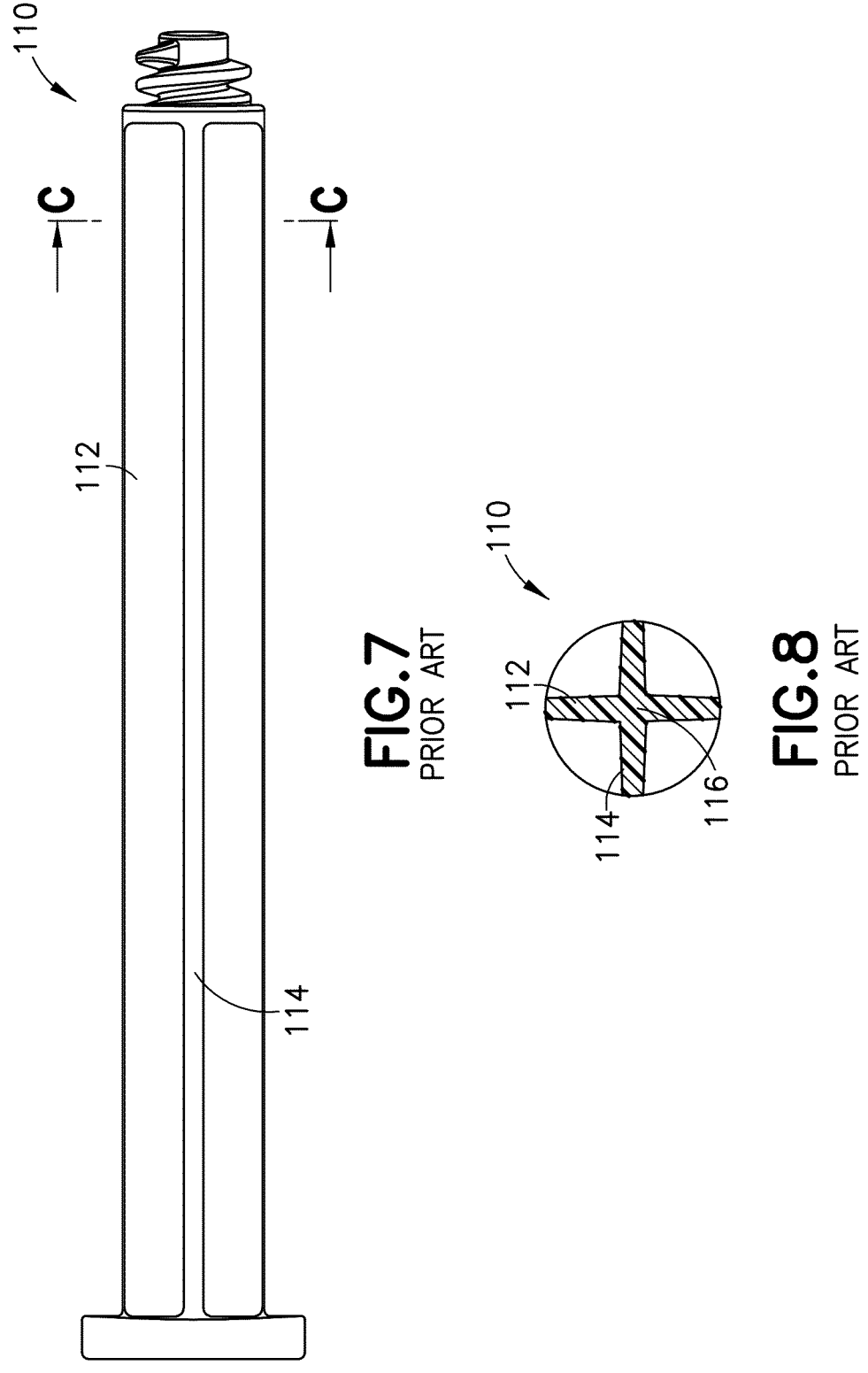
FIG. 7 is a side view of a prior art plunger rod.
FIG. 8 is a cross-sectional view of the plunger rod of FIG. 7, taken along line C-C of FIG. 7.

In operation, the geometry of plunger rod 10 provides it with a number of advantages over known plunger rods (e.g., without limitation, plunger rod 110, shown in FIGS. 7 and 8). For example, by having a discontinuous arcuate outer perimeter 40, and having sections that do not intersect each other, elongated body 12 can advantageously be manufactured using less material than a conventional plunger rod 110. As shown in FIG. 8, a conventional plunger rod 110 has a first planar portion 112 and a second planar portion 114 that intersects first planar portion 112 at a central region 116. In other words, the elongated body of plunger rod 110 is generally cross-shaped, having two planar portions 112, 114 that intersect each other at central region 116. It can readily be appreciated that central region 116 has an undesirably large amount of material due to the intersection of the first and second planar portions 112, 114. This is disadvantageous at least for the following reasons. One, by having a large amount of material in this region, material costs are relatively high to manufacture plunger rod 110 to the increased amount of material present within this region. Two, cycle times associated with molding plunger rod 110 are relatively long, due to the time required for the large central region 116 to cool.

The inventive plunger rod 10 of the present application solves these problems. First, by having material spaced around central axis 14 but void at the central axis 14, and being devoid of intersecting or overlapping regions which might otherwise generate large masses of material, costs can be reduced. In addition, plunger rods 10, 80 having the inventive structure described herein are able to resist breakage with better resistance to flexion (e.g., displacement away from central axis 14) during movement within the syringe barrel 4) than conventional plunger rods 110, and are able to do so using significantly less material. Due to the increased resistance to breakage, plunger rods 10, 80, unlike plunger rod 110, may be manufactured out of different materials (e.g., without limitation, thermoplastic material such as a polycarbonate material, polypropylene, polystyrene, etc.).

Cycle times associated with manufacturing plunger rod 10 (e.g., and plunger rod 80) are advantageously able to be reduced due to the elimination of relatively thick regions that might otherwise require long periods of time to cool during molding. Additionally, although less material is being used with plunger rods 10, 80, structural and functional integrity are advantageously not compromised due to the improved geometry. Specifically, while less material is used to manufacture plunger rods 10, 80, the improved shape, as shown in FIG. 6, provides beneficial stability to assist during movement into and out of syringe barrel 4. The improved shape maintains the functional attributes necessary to performing the plunging operations, but advantageously allows for a significant reduction in material costs, and cycle time. Moreover, curved end faces 20, 22 and intermediate face 30, in one example embodiment, are substantially evenly spaced from one another along the arcuate outer perimeter 40 of elongated body 12. Furthermore, by being angular, angular faces 32, 34 advantageously define three substantially equal-sized portions of elongated body 12, when viewed from the perspective of FIG. 6.

Table 1, reproduced below, shows 3D modeling data for different plunger rods, including a prior art "X section" plunger rod, and several "Ω section" plunger rods in accordance with the disclosed concept (e.g., plunger rods 10, 80), wherein "Ω" denotes the general cross-sectional shape of plunger rods 10, 80, as shown in FIG. 6. The "Thickness" is the largest thickness of the section of the PR (measured at the cross central point for the X section PR, and measured at the roundish shapes zones of the Ω section PR). In entries 3 to 6, "T" is the thickness of the PR of entry 2. The section surface is measured anywhere on the PR except where there are ribs. The compression and flexion displacements have been calculated with numerical simulation in response to an axial effort of 10 N. Table 1 presents various configurations studied, wherein #1 is the current X standard, #2 to #5 correspond to Ω profile with various combinations of thickness and number of ribs, and #6 is configuration of an S profile. Table 1 reflects technical information such as section surface (different than flange surface), and main usage outcome (applicable force via an index with X shape base 100).

Figure 9:
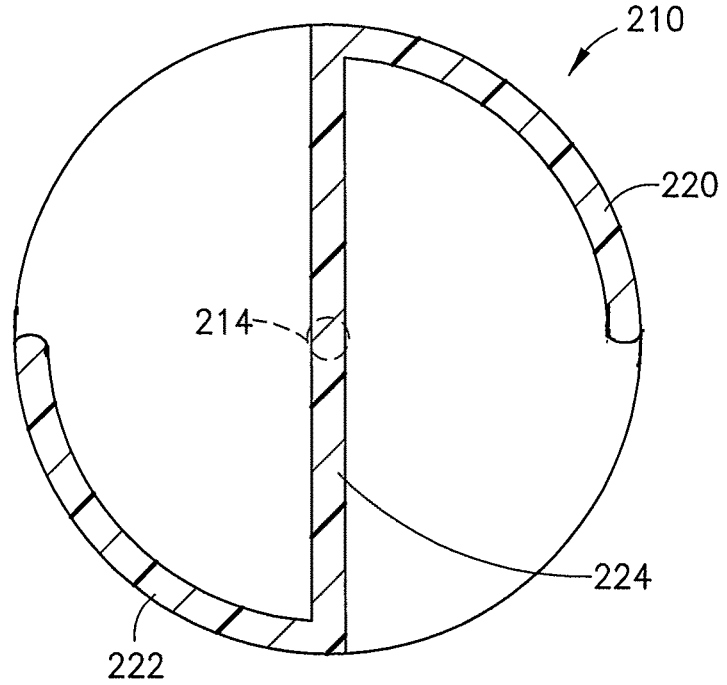
FIG. 9 is a cross-sectional view of another plunger rod that may be used with the syringe of FIG. 1, in accordance with another non-limiting aspect of the disclosed concept.

In another example embodiment of the disclosed concept, shown in FIG. 9, joining portion 224 intersects central axis 214 and extends directly from first curved end face 220 to second curved end face 222. In the embodiment of FIG. 9, the elongated body of plunger rod 210 has a generally S-shaped cross section. It will be appreciated that plunger

TABLE 1

| # | Model | Thickness (mm) | Section Surface (mm²) | Volume (mm3)* | Compression displacement (mm) | Flexion displacement (mm) | Applicable Force Index (no unit) |
|---|---|---|---|---|---|---|---|
| 1 | X section | 1.15 | 14.1 | 1345 | 0.037 | 2.50 | 100 |
| 2 | Ω section PR 2 Ribs | 1.10 | 27.1 | 2215 | 0.019 | 0.82 | 306 |
| 3 | Ω section PR 2 Ribs- 0.5 T | 0.58 | 15.0 | 1421 | 0.035 | 1.28 | 196 |
| 4 | Ω section PR 1 Rib - 0.5 T | 0.58 | 15.04 | 1414 | 0.035 | 1.28 | 196 |
| 5 | Ω section PR 2 Ribs - 0.4 T | 0.40 | 10.54 | 1120 | 0.050 | 1.73 | 145 |
| 6 | S section PR 2 Ribs - 0.7 T | 0.81 | 14.14 | 1385 | 0.032 | 3.00 | 83 |

*Volume includes the elongated body, the ribs, the flange and the threaded section.

Table 2, reproduced below, presents the same configuration as Table 1, with % variation versus reference X shape. This allows for an easy comparison from configuration to configuration.

Configuration 2 is 3 times more resistant to thumb force for only 14% price increase. This is very high performance for limited cost increase. Configuration 3 and 4 are 2 times more resistant to force and 17% saving. This is a high performance for lower cost. Configuration 5 is 45% more resistant versus X shape #1 for 25% lower cost. This is an improved performance for very low cost. Configurations 3 and 4 show that the number of ribs have no significant impact on performance for this size. Configuration 6 shows slightly lower performance for limited cost saving. This solution is dedicated to specific application and size, typically plunger rods having a small section.

rod 210 otherwise functions substantially the same as plunger rods 10, 80, discussed above, and provides the same improvements over prior art plunger rod 110 (e.g., reduced material costs, lower cycle time during molding).

Elements of one disclosed aspect can be combined with elements of one or more other disclosed aspects to form different combinations, all of which are considered to be within the scope of the present concept.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or

TABLE 2

| # | Model | | Normal and Tangent Displacements for 10N Force on Master Point | | | | | | |
|---|---|---|---|---|---|---|---|---|---|
| | | Thickness | Section Surface | Volume | Compression displacement | Flexion displacement | Force applicable | Price variation | Main characteristics |
| 1 | X section | Reference | Reference | Reference | Reference | Reference | Reference | Reference | Reference |
| 2 | Ω section PR 2 Ribs | −4% | 92% | 65% | −49% | −67% | 206% | 14% | Very high performance for limited cost increase |
| 3 | Ω section PR 2 Ribs- 0.5 T | −50% | 6% | 6% | −5% | −49% | 96% | −17% | High performance for lower cost |
| 4 | Ω section PR 1 Rib - 0.5 T | −50% | 6% | 5% | −5% | −49% | 96% | −17% | Better performance for low cost |
| 5 | Ω section PR 1 Rib - 0.4 T | −65% | −26% | −17% | 35% | −31% | 45% | −25% | Improved performance for very low cost |
| 6 | S section PR 2 Ribs - 0.7 T | −30% | 0% | 3% | −14% | 20% | −17% | −9% | Dedicated to specific application | customary practice in the art to which this disclosure pertains and which fall within the limits of the appended claims.

What is claimed is:

1. A plunger rod for use with a syringe having a syringe barrel, the plunger rod comprising:

an elongated body having a proximal end, a distal end opposite the proximal end, and a central axis extending between the proximal end and the distal end, a first curved end face, a second curved end face, and a joining portion joining the first curved end face to the second curved end face, each of the first curved end face, the second curved end face, and the joining portion extending between the proximal end and the distal end, wherein the first curved end face and the second curved end face together are comprised in a circle defined at least partially by a discontinuous arcuate outer perimeter of the elongated body, wherein the joining portion comprises an intermediate face, a first connecting face extending from the intermediate face to the first curved end face, and a second connecting face extending from the intermediate face to the second curved end face, wherein the intermediate face, the first curved end face, and the second curved end face are comprised in the circle delimited by the outer perimeter of the elongated body together therewith, and wherein the first curved end face and the second curved end face do not form a continuous portion of the outer perimeter of the elongated body.

2. The plunger rod according to claim 1, wherein the first connecting face is a first angular face with respect to the intermediate face, and wherein the second connecting face is a second angular face with respect to the intermediate face.

3. The plunger rod according to claim 2, wherein the first angular face and the second angular face each extend from the intermediate face at respective angles that are equal or greater than 90 degrees with respect to the intermediate face.

4. The plunger rod according to claim 1, wherein the first curved end face, the second curved end face, and the joining portion do not intersect the central axis of the elongated body.

5. The plunger rod according to claim 1, wherein the plunger rod further comprises a number of support ribs extending from the elongated body between the proximal end and the distal end.

6. The plunger rod according to claim 1, wherein the arcuate outer perimeter is concave facing toward the central axis.

7. The plunger rod according to claim 1, further comprising a stopper overmolded onto the elongated body.

8. The plunger rod according to claim 1, wherein the first connecting face is a first angular face with respect to the intermediate face, and wherein the second connecting face is a second angular face with respect to the intermediate face and wherein the first angular face and the second angular face each extend from the intermediate face at respective angles that are less than 120 degrees with respect to the intermediate face.

9. A plunger rod for use with a syringe having a syringe barrel, the plunger rod comprising:

an elongated body having a proximal end, a distal end opposite the proximal end, and a central axis extending between the proximal end and the distal end, a first curved end face, a second curved end face, and a joining portion joining the first curved end face to the second curved end face, each of the first curved end face, the second curved end face, and the joining portion continuously extending from the proximal end to the distal end of the elongated body, wherein the first curved end face and the second curved end face together are comprised in a circle defined at least partially by a discontinuous arcuate outer perimeter of the elongated body defined by a diameter of the distal end of the elongated body, and wherein the joining portion intersects the central axis and extends directly from the first curved end face to the second curved end face.

10. The plunger rod according to claim 9, wherein the elongated body has a generally S-shaped cross section.

11. The plunger rod according to claim 9, wherein the plunger rod further comprises a number of support ribs extending from the elongated body between the proximal end and the distal end.

12. The plunger rod according to claim 9, wherein the joining portion intersects the central axis and extends in a straight line directly from the first curved end face to the second curved end face.

13. A syringe assembly comprising:

a syringe barrel having a sidewall, a distal end, and a proximal end; and a plunger rod comprising:

an elongated body having a proximal end, a distal end opposite the proximal end of the elongated body, and a central axis extending between the proximal end of the elongated body and the distal end of the elongated body, a first curved end face, a second curved end face, and a joining portion joining the first curved end face to the second curved end face, each of the first curved end face, the second curved end face, and the joining portion extending between the proximal end of the elongated body and the distal end of the elongated body, wherein the first curved end face and the second curved end face together are comprised in a circle defined by a discontinuous arcuate outer perimeter of the elongated body, wherein the joining portion comprises an intermediate face, a first connecting face extending from the intermediate face to the first curved end face, and a second connecting face extending from the intermediate face to the second curved end face, and wherein the intermediate face, the first curved end face, and the second curved end face are comprised in the circle delimited by the outer perimeter of the elongated body together therewith, and wherein the first curved end face and the second curved end face do not form a continuous portion of the outer perimeter of the elongated body.

14. The syringe assembly according to claim 13, wherein the first connecting face is a first angular face with respect to the intermediate face, and wherein the second connecting face is a second angular face with respect to the intermediate face.

15. The syringe assembly according to claim 14, wherein the first angular face and the second angular face each extend from the intermediate face at an angle equal or greater than 90 degrees with respect to the intermediate face.

16. The syringe assembly according to claim 13, wherein the first curved end face, the second curved end face, and the joining portion do not intersect the central axis of the elongated body.

17. The syringe assembly according to claim 13, wherein the plunger rod further comprises a thumb press disposed at the proximal end of the elongated body, and wherein the thumb press is wider than the syringe barrel.

18. The syringe assembly according to claim 13, wherein the plunger rod further comprises a coupling portion disposed at the distal end of the elongated body; and wherein the syringe assembly further comprises a stopper coupled to the coupling portion and disposed internal with respect to the syringe barrel.

19. The syringe assembly according to claim 13, wherein the arcuate outer perimeter is concave facing toward the central axis.

20. The syringe assembly according to claim 13, wherein the first connecting face is a first angular face with respect to the intermediate face, and wherein the second connecting face is a second angular face with respect to the intermediate face and wherein the first angular face and the second angular face each extend from the intermediate face at respective angles that are less than 120 degrees with respect to the intermediate face.

21. A syringe assembly comprising:
a syringe barrel having a sidewall, a distal end, and a proximal end; and
a plunger rod comprising:
an elongated body having a proximal end, a distal end opposite the proximal end of the elongated body, and a central axis extending between the proximal end of the elongated body and the distal end of the elongated body,
a first curved end face, a second curved end face, and
a joining portion joining the first curved end face to the second curved end face,
each of the first curved end face, the second curved end face, and the joining portion continuously extending from the proximal end of the elongated body to the distal end of the elongated body,
wherein the central axis of the elongated body coincides with a corresponding central axis of the syringe barrel,
wherein the joining portion intersects the central axis of the elongated body and extends directly from the first curved end face to the second curved end face,
wherein the first curved end face and the second curved end face together at least partially constitute a circle defined by an arcuate outer perimeter of the elongated body.

22. The syringe assembly according to claim 21, wherein the plunger rod further comprises a thumb press disposed at the proximal end of the elongated body, and wherein the thumb press is wider than the syringe barrel.

23. The syringe assembly according to claim 21, wherein the plunger rod further comprises a coupling portion disposed at the distal end of the elongated body; and wherein the syringe assembly further comprises a stopper coupled to the coupling portion and disposed internal with respect to the syringe barrel.

24. The syringe assembly according to claim 21, wherein the elongated body has a generally S-shaped cross section.

25. The syringe assembly according to claim 21, wherein the joining portion intersects the central axis of the elongated body and extends in a straight line directly from the first curved end face to the second curved end face.

* * * * *